United States Patent [19]

Linkow et al.

[11] Patent Number: 4,531,917
[45] Date of Patent: Jul. 30, 1985

[54] DETACHABLE POST FOR AN OSSEOUS IMPLANT

[76] Inventors: Leonard I. Linkow, 1530 Palisade Ave., Fort Lee, N.J. 07024; Leo Hoffman, 15 Woodmere Blvd., Woodmere, N.Y. 11598

[21] Appl. No.: 595,984

[22] Filed: Apr. 2, 1984

[51] Int. Cl.³ .............................................. A61C 8/00
[52] U.S. Cl. .................................................... 433/176
[58] Field of Search ................................. 433/173–176

[56] References Cited

U.S. PATENT DOCUMENTS 4,187,609 2/1980 Edelman ............................ 433/176
4,283,176 8/1981 Vajda .................................. 433/173

*Primary Examiner*—Robert Peshock
*Attorney, Agent, or Firm*—Darby & Darby

[57] ABSTRACT

An oral implant for supporting an artificial tooth structure includes an implant portion which is buried in the bone of the patient along the occlusal plane. A neck portion extends from the side of the implant portion remote from the groove and receives a post portion on which the artificial tooth structure is cemented. Means are provided on the neck portion so as to cause it to become wedged within a cavity of the overlying post portion, thereby releasably locking the post to the neck portion. As a result of this arrangement, a bridge structure can be removed from an implant without having to destroy the bridge.

14 Claims, 14 Drawing Figures

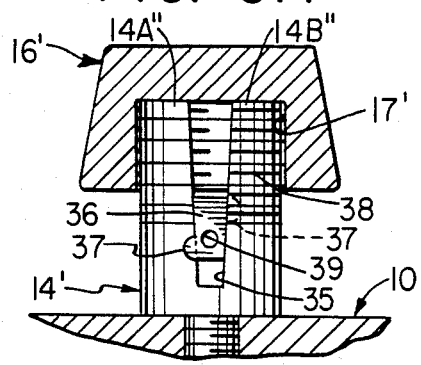
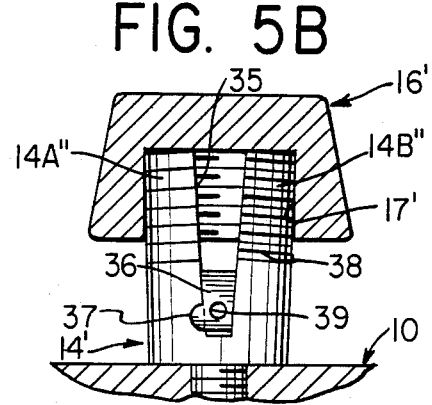
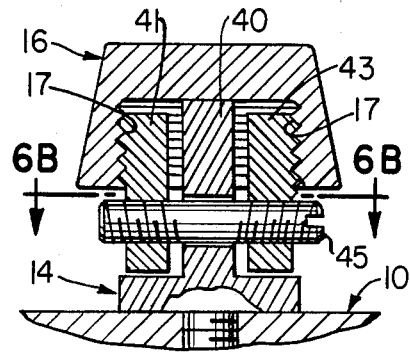
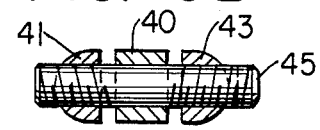
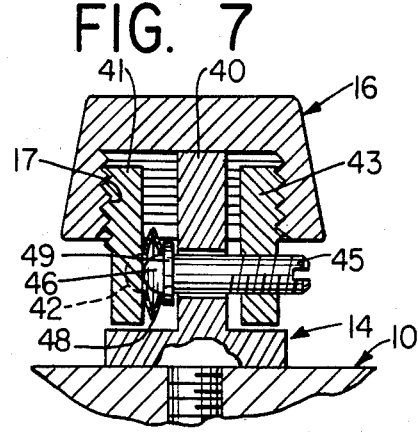
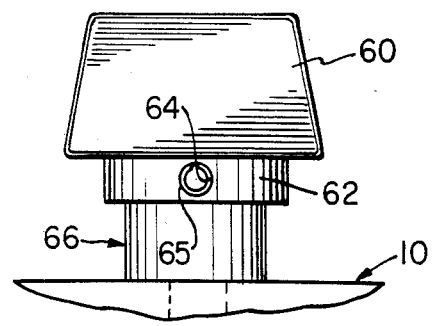
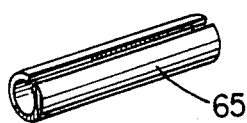

DETACHABLE POST FOR AN OSSEOUS IMPLANT

BACKGROUND OF THE INVENTION

This invention relates to dental implants and, more particularly, to detachable posts for implants.

A dental implant, such as that described in U.S. Pat. No. 3,465,441 and U.S. Pat. No. 3,660,899 of Dr. Leonard I. Linkow are used to support an artificial bridge, tooth or other dental prosthesis. The implant has an implant portion, e.g. in the form of a blade, that is secured in the underlying bone in an edentulous span. A linking or neck portion, e.g. in the form of a screw thread, extends up from the implant portion and is attached to a support or post portion on which the artificial bridge or crown is attached. This type implant is inserted by making an incision in tha fibromucosal tissue down to the underlying alveolar ridge crest bone. The tissue is then reflected to expose the bone and a burr is used to create a groove in the bone which is as deep as the implant portion. Using a mallet, the implant portion is tapped into the bone. After the insertion, the tissue is sutured about the neck portion so that the post protrudes above the tissue line. Typically, a few weeks or months are allowed to pass before the dental prosthesis is attached to the post. During this period, bone starts to grow around the implant portion and through holes provided in it, thereby acting to anchor the implant in place before it is stressed by use.

Submergible blade implants, such as that shown in U.S. Pat. No. 4,177,562 of A. L. Miller and A.J. Viscido, allow a blade to be inserted in the jawbone for a long period of time before being placed in actual use. With this type of implant, the blade is completely submerged in the bone. It is then covered over and allowed to remain in place for several months. Once there has been substantial regrowth of the bone around and through the submerged blade, the tissue is again opened and an integral neck and post assembly is attached to the blade by a typical screw connection.

Removable posts, such as the screw type shown in U.S. Pat. No. 3,660,899 or U.S. Pat. No. 4,177,562, are necessary with submergible implants which are to remain out of use for a period of time while the bone regrows. Screw posts are also useful with non-submergible implants because they allow a good blade to remain in place when a defective bridge is removed. This is accomplished by cutting the bridge into sections in order to allow the post to be turned for removal of the post from the blade. In some cases, however, it is the blade which is defective. Nevertheless, current practice requires that the perfectly good bridge, which is permanently cemented over the posts, be destroyed in order to allow the posts to be unscrewed and the defective implant blade replaced.

SUMMARY OF THE INVENTION

The present invention is directed to providing posts, at least a portion of which are detachably connected to the implant portion in such a manner that a bridge need not be destroyed in order to remove it from the implant.

In an illustrative embodiment of the invention, the oral implant includes an implant portion, e.g. a blade, adapted to be fitted in an opening prepared in the jawbone. This implant portion has at least one location along its length where a neck is attached to it. The neck in turn is connected to a post which has an artificial crown or bridge cemented to it. The neck portion of the assembly can be unitary with the implant or screwed into it. In turn the post portion is connected to the neck by some form of wedging action.

In one embodiment, the neck portion has a vertical split that divides a portion of the neck into two segments that fit loosely within a cavity in the post. A small screw is insertable at the base of the split and causes the neck segments on each side of the split to spread and to wedge tightly within the post cavity. If the screw is withdrawn, the neck segments can be squeezed together to allow the post, and the bridge which is cemented to it, to be removed from the neck.

In a variation of this technique, a wedging piece is substituted for the screw. It is positioned in a groove between segments of the neck so as to force them outwardly. Tabs located on both sides of the wedging piece keep it from falling out of place. With this arrangement, the post is screwed onto the neck after the wedge is inserted in the groove between the neck segments and then the wedge is moved in the groove to spread the neck segments to firmly lock the post in place on the neck.

Another embodiment uses a neck structure with separate lateral segments attached to a primary neck portion. A shaft passes through the primary portion and is threadably connected to the lateral segments by respective left-hand and right-hand threads. When the shaft is turned in one direction, the lateral segments move closer to the primary neck portion and when it is turned in the other direction, they move away from the primary neck portion and into wedging contact with the interior cavity of the overlying post.

A still further embodiment also has the post connected to the neck by separate lateral segments positioned on a shaft. The shaft passes through the primary neck portion and a reduced area, disk-shaped, portion at one end enters a corresponding recess in one of the segments. The other end of the shaft is threaded into the other segment. By turning the shaft in one direction, the shaft is withdrawn toward the segment in which it is threaded and the segments are allowed to come closer together. Turning the shaft in the other direction forces the segments apart and into wedging contact with the cavity in the overlying post. While this is happening the disk-shaped end can cam out of the recess in the lateral segment which it contacts until further separation of the lateral segments is prevented by contact with the walls of the cavity in the post. Then a spring or the natural resilience of the material allows the disk end to be rotated sufficiently to snap into and be locked by the recess in the lateral segment. This locking action prevents the shaft from turning, thereby keeping the post from coming loose.

In another embodiment of the invention an aperture is provided in the neck, which aperture aligns with another aperture in a collar extending from the base of the post. A spring roll pin is compressed, inserted into the two aligned apertures and released. The expansion of the spring roll pin wedges it in the aperatures where it holds the post on the neck.

The mesial and distal surfaces of the neck assembly and the walls of the post cavity where the wedging action occurs, are both supplied with grooves or threads. These grooves or threads intermesh with each other when the post is wedged on the neck so that a secure connection is achieved.

BRIEF DESCRIPTION OF THE DRAWINGS

The foregoing and other features of the present invention will be more readily apparent from the following detailed description and drawings of illustrative embodiments of the invention in which:

FIG. 5A is an enlarged side view of an embodiment of the invention utilizing a wedging piece before the segments of a neck have been spread, and FIG. 5B shows the same implant neck with the segments spread;

FIG. 6A is a side sectional view of an alternative embodiment of the present invention utilizing a shaft with two opposite sets of threads and FIG. 6B is a top sectional view along line A—A of the structure in FIG. 6A;

FIG. 7 is a side view of an embodiment of the invention utilizing a shaft with one set of threads;

FIG. 8 is a top view of the shaft end used in the embodiment of FIG. 7.

FIG. 9 shows an embodiment of the invention wherein a spring roll pin is wedged in apertures in the neck and post so as to hold them together; and FIG. 10 is an enlarged view of a spring roll pin.

DESCRIPTION OF ILLUSTRATIVE EMBODIMENTS

Figure 1:
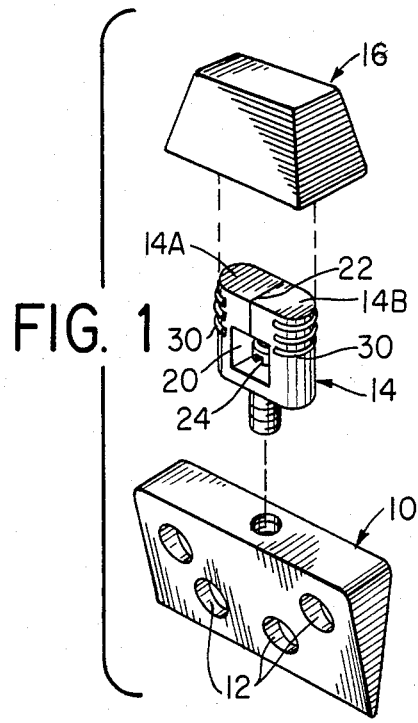
FIG. 1 is an exploded perspective view of a detachable post type osseous implant utilizing a vertical wedging screw according to the present invention.

In FIG. 1 there is shown a greatly enlarged embodiment of an osseous implant according to the invention and suitable for use in an edentulous span in the alveolar ridge crest of patients. This implant includes an implant portion 10 in the form of a blade which may be made from titanium, vitalium, surgical stainless steel or other typical implant material. This blade has holes or vents 12 through it which allow bone to grow completely through the blade so as to anchor the implant in place. As an alternative, the implant portion can be a screw implant or other common implant device.

Extending upwardly from the blade portion 10 is a neck portion 14 having an elliptically-shaped cross section. However, it could also have a round, square, rectangular or other cross-sectional shape. Neck 14 may be unitary, i.e. one piece with the blade, or it may be screwed onto the blade as shown in FIG. 1. In turn, neck portion 14 fits within a cavity 17 of a post 16. As will be described in more detail below, means are provided for detachably connecting neck 14 and post 16.

One method of attaching post 16 to neck 14 is shown in FIGS. 1 and 2. In these drawings, the neck has two segments 14A and 14B which extends from the base of the post like projecting legs. Ordinarily the segments are in mating contact with each other along a split line 22. However, there is a cut-out 20 in the neck where a threaded aperture 23 is positioned at the split line 22. A screw 24 is inserted into this threaded aperture 23 by means of a tool, such as Allen wrench 26. The movement of screw 24 into the aperture 23 causes segments 14A and 14B to separate from each other and to spread apart. This movement causes the segments to come into wedging contact with the mesial and distal walls of the cavity 17 in post 16, thereby securely holding post 16 on neck 14. In order to improve the holding action, threads or grooves 30 are located on the mesial and distal ends of neck 14 and these are received in corresponding recesses 32 in the cavity 17 of post 16 so as to interlock these structures.

An artificial bridge or crown (not shown) can be cemented onto post 16. If for some reason it is necessary to remove the bridge from the implant, this can be accomplished by again using Allen wrench 26 to turn screw 24. In this case however, it is withdrawn from between the segments 14A and 14B. Then a pair of pliers or a similar tool is used to squeeze the segments together again so that the post and the attached bridge can be lifted off the neck.

The split line 22 between the segments of the neck divide the neck in the bucco-palatal or labio-lingual directions. In the design of FIG. 2 the threads or grooves are only on the mesial and distal surfaces and not the labial/buccal or lingual/palatal surfaces because the neck is elliptical in shape, and not round or square. Thus the post of FIGS. 1 and 2 has internal threads or grooves only along the mesial and distal walls of its cavity 17 and not along the labial/buccal or lingual/palatal walls.

Figure 2A:
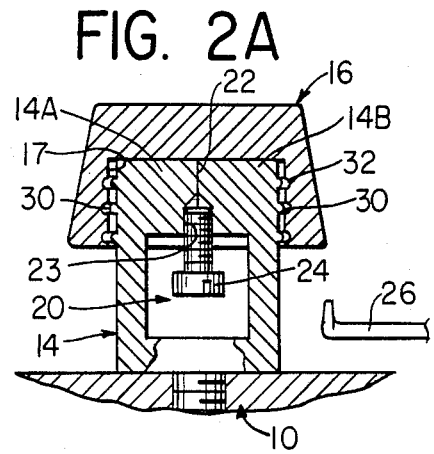
FIG. 2A is an enlarged side view of the neck portion of an implant similar to that in FIG. 1 before its segments have been spread.

During the connection of the post to the neck as shown in particular in FIG. 2A, the set screw 24 moves against an inclined surface 21 of the aperture 23 to cause the spreading action. After the segments have been spread slightly, the post can be gently tapped onto the neck portions. Then the screw is turned further into threaded aperture 23 against the inclined surfaces 21 to achieve further spreading of the segments and wedging of the post on the neck.

Figure 3:
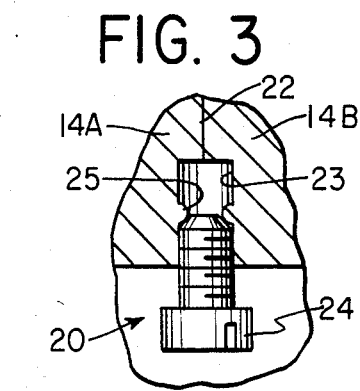
FIG. 3 is a variation on the embodiment of FIG. 2A.

As an alternative, small projections 25 can be provided on the interior of the aperture 23 in place of the inclined walls 21. This is shown in more detail in FIG. 3. With such an arrangement, the screw contacts the projections to spread the neck segments. One advantage of this alternative is that the screw does not have to be removed in order for the post to be unlocked from the neck. Instead, the post is locked and unlocked when the screw is turned a half or full thread beyond or before the internal projections 25, respectively. This allows the neck segments to be squeezed together even with the screw in the aperture, and allows spreading and closing of the segments with only a minor amount of turning of the screw.

Figure 4B:
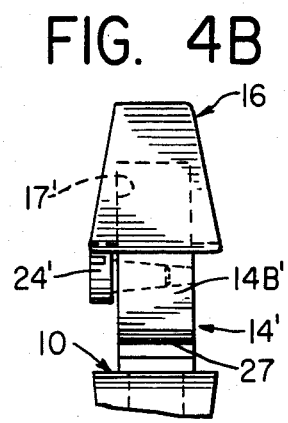
FIGS. 4A and 4B are side and end views, respectively, of an embodiment of the invention utilizing a horizontal wedging screw instead of the vertical wedging screw shown in FIG. 2.
Figure 2B:
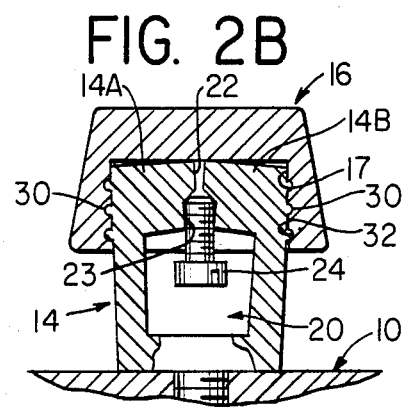
FIG. 2B is an enlarged sectional side view of the neck portion of the same implant after its segments have been spread.
Figure 4A:
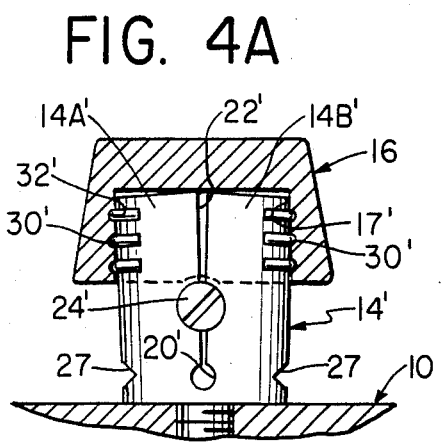

FIGS. 4A and 4B show a modification of the arrangement shown in FIGS. 2A and 2B. In this arrangement, neck 14' is also provided with two upwardly extending legs or segments 14A' and 14B'. However, with this embodiment, the set screw 24' is received in a horizontal aperture between the segments, and not a vertical aperture as in FIG. 2. Also, the opening 20' is made round and smaller than opening 20 in FIG. 2. It can be made smaller because it is no longer necessary for it to be wide enough to accommodate the tool 26, since screw 24' is reached from the side of the neck. This is a particular advantage because access to screw 24' is much simpler with this embodiment than with that of FIG. 2. The opening 20 is not eliminated altogether, however, because it makes the segments more flexible. Also, notches 27 are made in the neck adjacent the opening 20' to accommodate pliers or similar tools used to squeeze the segments together when the screw 24' is removed, and the post and neck are detached from each other.

In the embodiment of FIGS. 5A and 5B, the two segments are not in contact with each other under normal circumstances. Instead a groove 35 is provided between them and a small wedge piece 36 is installed in this groove 35. The segments 14A″ and 14B″ form portions of a circle and have threads 38 located about them. The interior cavity 17' of a post 16' also has matching threads so that it may be screwed onto the neck after the wedge piece 36 has been put in place. It should be noted that the neck portion shown in FIGS. 1 and 2 has a generally oval or elliptical cross-section, but it could also be made with a round cross-section as in the neck of FIG. 5.

Once the post 16' has been screwed onto the threads 38 of neck 14″, the wedge piece 36 can then be tapped lower in the groove 35 between the segments. As a result, the segments are spread further apart and lock the post on the neck.

In order to ensure that the wedge piece 36 does not fall out of the groove 35 before it is firmly wedged in place, wedge piece 36 is provided with tabs 37. One tab is located on one side of the wedge piece near the bottom and the other is located near the top on the other side. Further, to assist in moving the wedge piece down in groove 35, a small aperture 39 may be provided in the wedge piece. A tool can be inserted in this aperature in order to make it easier to tap the wedge piece lower in the groove when the post is being locked to the neck, or to tap it out of the groove when it is desired to remove the post from the neck.

With the embodiment of FIG. 5, the wedge piece 36 is removed to permit detachment of the post from the neck by using a burr or other grinding tools to remove at least one tab 37. With the tab removed the wedge piece can be tapped horizontally from between the neck segments and the segment squeezed together. After the wedging force is released, a pair pliers or similar tool is used to squeeze the segments of the neck together. Thus, the post may be slipped off the threaded portions of each of the posts which are used to anchor the bridge, and the entire bridge can be removed in one piece.

Once the bridge is removed, a failing blade can then be removed, and can be immediately replaced with another one. Alternatively, a three or four month waiting period is observed so that new bone grows in the denuded groove which previously held the blade. Then a new groove is made and the blade portion installed in it. The old post and bridge are then installed on the new implant.

Another embodiment of the invention is shown in FIGS. 6A and 6B. In this arrangement, the neck has a central portion 40 and two separate lateral or side portions 41, 43. A shaft 45 passes through central neck portion 40 without engaging it. However, it is threadably engaged with the side portions 41 and 43. The shaft has right-hand threads where it engages one of the side portions and left-hand threads where it engages the other. As a result, turning the shaft in one direction will cause the side portions 41, 43 to come closer together, and turning it in the other direction will cause them to spread away from each other and to come into wedging contact with the interior side walls of the cavity 17 of post 16.

An arrangement similar to FIG. 6 is shown in FIG. 7. In this arrangement, the neck again has a central portion 40 and side portions 41 and 43. Further, it has a shaft 45' which passes through central portion 40 without engaging it. However, unlike shaft 45, shaft 45' has only one set of threads and engages only side member 43. The other end 46 of the shaft has a disk-shaped projection which fits within a recess or slot 42 in side member 41.

As shaft 45' is rotated, it extends more and more from side member 43, passes through central portion 40 and abuts against side member 41. Before the side members 41, 43 come into locking engagement with post 16, the disk portion 46 can ride up out of recess 42 as shaft 45 is turned. However, when the side members wedge against the interior of the cavity in post 16, disk-shaped projection 46 becomes locked in recess 42 such that the shaft cannot unscrew due to vibrations within the patient's mouth. Just prior to this locking engagement, the structure must be stressed in order for the portion 46 to align itself with slot 42. In most cases, the natural resilience of the material of the post and neck is sufficient for this purpose. However, if necessary a spring, such as Belleville washer 48, can be installed on the shaft to allow the additional play needed to accomplish this locking connection.

The spring 48 is located between segment 41 and a flange 49 (FIG. 8) at end 46 of the shaft 45'. As a result, the spring acts to push segment 41 into wedging contact with post 16 while it is being compressed by the shaft. The final turn of shaft 45' is accomplished by further compression of this spring. To loosen the connection the shaft must be turned firmly in the opposite direction so that the structure is stressed or the spring compressed enough for the disk portion 46 to cam out of recess 42.

The post 60 shown in FIG. 9 has a depending collar 62 that defines an aperture 64. Aperture 64 extends into a similar aperture in neck 66. A roll spring pin 65 (FIG. 10) is compressed and wedged into these aligned apertures so as to hold the post on the neck.

One unique feature of this invention is that the bridge, which is cemented over the post permanently, can be be removed from the implant to replace a failing implant blade. The bridge need not be destroyed, as is required with presently known designs. Instead, the post is detached from the neck portion or portions. This is accomplished by removing the vertical or horizontal screws, pins or wedging piece used to achieve the wedging connection between the post and the neck.

If any of the crowns should cover the horizontal or vertical screw heads used to bring about the wedging connection between the neck and the post, a tiny hole can be made in the crown to reach the screw. This hole can later be refilled with one of the composite materials available today, making the tiny opening practically invisible.

While the invention has been particularly shown and described with reference to preferred embodiments thereof, it will be understood by those skilled in the art that various changes in form and details may be made therein without departing from the spirit and scope of the invention.

We claim:

1. An oral implant for supporting an artificial tooth structure comprising:
    an implant portion adapted to be fitted in an opening in a bone in the vicinity of the occlusal plane, which bone has been exposed by an incision in the covering fibromucosal tissue;

a neck portion extending from a part of the implant portion toward the occlusal plane;

a post portion having an interior cavity with side walls being adapted to fit over an end of said neck portion directed toward the occlusal plane; and wedging means for causing said neck portion to spread apart such that said neck portion comes into engagement with the interior cavity of said post portion so said post is releasably locked to said neck.

2. An oral implant as claimed in claim 1 wherein part of said neck portion is divided into two extending segments, and wherein said wedging means comprises a screw which is threaded into an aperture between said segments such that insertion of the screw causes the segments to spread apart and to come into wedging contact with side walls of the cavity of said post portion.

3. An oral implant, as claimed in claim 2 wherein the threaded aperture includes inclined surfaces on the segments which are adapted to be contacted by the screw and act to force the segments apart.

4. An oral implant as claimed in claim 2 wherein the threaded aperture includes projections on the segments which are adapted to be contacted by the screw and act to force the segments apart.

5. An oral implant as claimed in claim 2 wherein the post segments form an elliptical cross-section, the neck is divided into segments in the buccal-lingual direction, and there are corresponding and interlocking grooves and projections on the mesial-distal side walls of the segment and the post cavity, respectively.

6. An oral implant as claimed in claim 1 wherein the neck portion is divided into two extending segments with a groove between them, and wherein said wedging means is a member inserted in the groove such that movement of the member along the groove causes the segments to spread into wedging engagement with the side wall of the cavity of said post portion.

7. An oral implant as claimed in claim 6 wherein said member has tabs at its edges to prevent said member from sliding out of said groove.

8. An oral implant as claimed in claim 6 wherein the segments form a circular cross-section, the segments have screw threads, and the side walls of the post cavity have matching screw threads such that said post may be screwed onto said neck after the member is in place in the groove.

9. An oral implant as claimed in claim 1 wherein said neck portion comprises a central section and two separate side sections, one of said side sections being located on each side of said central section; and wherein said wedging member comprises a shaft passing through said central section and being in threaded engagement with said side sections, said shaft having right-hand threads where it engages one of the side sections and left-hand threads where it engages the other, such that rotation of said shaft will cause the side sections to move away from each other and to come into wedging contact with the side walls of the cavity of the post.

10. An oral implant as claimed in claim 9 wherein said side sections and the side walls of the cavity of the post have corresponding and interlocking grooves and projections, respectively.

11. An oral implant as claimed in claim 1 wherein said post includes a central section and two separate side sections, one of said side sections being located on each side of said central section; and wherein said wedging member comprises a shaft passing through said central section and having one end in threaded engagement with one of said side members, the other end of said shaft having a projection for engagement with a slot in the other side member, such that rotation of the shaft will cause the side members to come into wedging engagement with the side walls of the cavity of the post and will cause the projection to be lockably engaged in the slot.

12. An oral implant as claimed in claim 11 wherein said end sections and the side walls of the cavity of the post have corresponding and interlocking grooves and projections, respectively.

13. An oral implant as claimed in claim 11 further including a spring between a flange on the other end of the shaft where the projection is located and the other side member, said spring permitting the projection of the shaft to cam out of the recess in the side section slot until there is a firm connection between the neck and the post, and thereafter allowing the shaft to continue to rotate sufficiently to become locked in the slot in said side section.

14. An oral implant as claimed in claim 1 wherein said post includes a collar which fits over the neck, aligned apertures being provided in both the post collar and the neck; and wherein the wedging means comprises a roll spring pin adapted to be received in the apertures to hold the post on the neck.

* * * * *